(12) United States Patent
Longepied et al.

(10) Patent No.: US 8,697,231 B2
(45) Date of Patent: Apr. 15, 2014

(54) POROUS STRUCTURE HAVING A CONTROLLED PATTERN, REPEATED IN SPACE, FOR PRODUCING SURGICAL IMPLANTS

(75) Inventors: Patrice Longepied, Sceaux (FR); Guillaume Dubois, Vanves (FR)

(73) Assignee: OBL, Chatillon (FR)

( * ) Notice: Subject to any disclaimer, the term of this patent is extended or adjusted under 35 U.S.C. 154(b) by 51 days.

(21) Appl. No.: 13/394,856

(22) PCT Filed: Sep. 9, 2010

(86) PCT No.: PCT/FR2010/000614
§ 371 (c)(1),
(2), (4) Date: Apr. 2, 2012

(87) PCT Pub. No.: WO2011/030017
PCT Pub. Date: Mar. 17, 2011

(65) Prior Publication Data
US 2012/0177939 A1    Jul. 12, 2012

(30) Foreign Application Priority Data
Sep. 9, 2009 (FR) .................................... 09 04314

(51) Int. Cl.
*B32B 3/26* (2006.01)

(52) U.S. Cl.
USPC ............... 428/316.6; 428/304.4; 428/546; 623/23.53; 623/16.11

(58) Field of Classification Search
None
See application file for complete search history.

(56) References Cited

U.S. PATENT DOCUMENTS

| | | | |
|---|---|---|---|
| 6,709,739 | B1 | 3/2004 | Mullen et al. |
| 2005/0112397 | A1 | 5/2005 | Rolfe et al. |

FOREIGN PATENT DOCUMENTS

| | | |
|---|---|---|
| DE | 202006015415 | 11/2006 |
| EP | 1683593 A2 | 7/2006 |
| WO | 2008143661 A1 | 11/2008 |
| WO | 2009048314 A1 | 4/2009 |

OTHER PUBLICATIONS

International Search Report for PCT/FR2010/000614, dated Jan. 27, 2011.

*Primary Examiner* — Mark Ruthkosky
*Assistant Examiner* — Julia L Rummel
(74) *Attorney, Agent, or Firm* — EIP US LLP

(57) ABSTRACT

The present invention relates to a porous structure having a controlled pattern (1), which is repeated in space, in three dimensions, said porous structure enabling the production of surgical implants for filling in bone defects. According to the invention, said structure is characterized in that said pattern (1) consists of three wings (2) arranged in a star shape, each angle (A) formed between two wings being substantially equal to 120°, each wing having a generally rectangular shape and being hollowed (3) at the center thereof. Each of the three wings (2) of said pattern is advantageously beveled at its free end or tip (4), and the width of the base (5) of each bevel is slightly greater than the thickness of the wings (2) of which it forms an extension.

5 Claims, 4 Drawing Sheets

POROUS STRUCTURE HAVING A CONTROLLED PATTERN, REPEATED IN SPACE, FOR PRODUCING SURGICAL IMPLANTS

The present invention relates to a porous structure having a controlled pattern, which is repeated in space, in three dimensions, said porous structure enabling the production of surgical implants for filling in bone defects.

It is known to use implants to remedy the total or partial absence of bone or bone defects in humans or animals, these implants being made so as to have a porous structure imitating as much as possible that of bone.

The pores of the implant in fact enable the bone cells to multiply in said implant and thus to ensure a better load transfer between the bone and the implant, which has the effect of anchoring the latter strongly into the healthy neighboring parts of the bone to be repaired or filled in.

This will consequently result in a quicker healing process.

Classical implants are made of titanium, a material that is known to be biocompatible.

Many methods for making such implants of titanium and having a porous structure are already known.

The first method consists in making an implant whose shape itself and whose geometry correspond to the part of the bone that is to be filled in or repaired.

According to this first method, a prototype is made of wax and in a geometry corresponding exactly to the part of the bone to be filled in or repaired.

This prototype is then immersed in a refractory material and this assembly is heated in order to destroy the wax.

The remaining refractory material is then sintered at high temperature in order to obtain a mold. It is then only necessary to cast the molten titanium into this mold, which will then be destroyed by chemical solvents that do not attack the titanium.

Another related method consists in introducing titanium microbeads into the mold that has been made as has just been described and to cause these microbeads to become united to one another through electro spark alloying.

The flaw of these erstwhile methods, however, is that although the implants thus made each have the desired shape, they are however only a little or not at all porous and, in any event, it is impossible to dictate the size of the pores and, consequently, the implant's porosity value.

An improved method is based on the use of a paste constituted of titanium powder, of a water solution of methylcellulose and stearic acid. This paste is deposited in superimposed layers at the bottom of a tray in order to form the geometry of the required part. The assembly is then dried, then sintered under vacuum at high temperature, in order to obtain the finished part (*Biomaterials* 27 (2006) 1223-1235).

A similar process is based on the use of a paste constituted of titanium powder mixed with ammonium bicarbonate. The mixture is compressed into a mold under high pressure. The semi-finished product thus obtained is then brought to the desired shape by mechanical processing, for example by milling. Finally, in order to make the material porous, the mixture is heated to 80° C. This has the effect of melting the ammonium bicarbonate that escapes and makes way for the desired pores.

A variant of the latter method consists in sintering the mixture by bringing it to a temperature of 1300° C., such a sintering having the effect of making the atoms migrate and the titanium nuclei to bond to one another, which thus ensures the implant's strength.

Although the implants thus obtained by using these new methods are definitely porous, the fact remains that once again it is difficult to determine in advance the size and the shape of the pores, and thus to make an implant whose structure has a porosity as close as possible to that of the bone.

New methods, recently developed, make it possible to achieve much more satisfying results from this point of view.

By way of first examples, a method of bonding a titanium powder by means of an electron beam or a laser beam is used. These two methods are similar: only the used energy source is different, with the energy being supplied by the electrons in the first case and by the photons in the second case. In these two methods, a layer of titanium powder that is fused locally at the desired places is deposited at the bottom of a tray. To this effect, the geometry of the part to be made is virtually cut into slices. The first layer of powder corresponding to the first layer is deposited. The electron beam or the laser beam travels across this layer in order to bond the titanium powder according to the geometry of the part that should be obtained. A new layer of powder is then deposited on this existing and already treated one, and this new layer is also bonded at the necessary places. The process is thus repeated until the final part is obtained by layering layers bonded with one another (*Acta Biomaterialia* 4 (2008) 1536-1544 as regards the bonding of titanium powder by electron beam and *Biomaterials* 27 (2006) 955-963 as regards the bonding by laser beam).

A method slightly different from the preceding one, called LENS (Laser Engineered Net Shaping), makes it possible in fact to make parts by superimposing layers of titanium powder. In this LENS process, the powder here is supplied within a tuyere that expels the titanium powder at the exact place onto which the laser beam is directed. The molten titanium is then projected directly according to the geometry of the part to be manufactured (*Acta Biomaterialia* 3 (2007) 1007-1018).

Obtaining implants by using the LENS process is also described in international patent application published under reference number WO 2008/143661.

In all the methods recalled here above, the titanium powder that is not molten is eliminated at the end of the process so that the manufactured product should be "open", i.e. that it should comprise, between the molten places, pores and connections between pores that reproduce as closely as possible the characteristics of the bone.

An example of porous structure enabling the production of surgical implants is described in patent application US 2005/112397 published on 26 May 2005 in the name of Jonathan L. Rolfe et al. This porous structure is obtained by superimposing layers of a material such as titanium, wherein the layers are deposited in succession and are then each bonded to the preceding layer and to the immediately subsequent layer. Each layer has several through apertures, wherein said apertures match each other vertically from one layer to the next so that, in the end, the porous structure has a multiplicity of vertical shafts. However, since these shafts are, by virtue of their construction, parallel to one another, there can therefore be no connection between them. Therefore, the porous structure thus achieved has a porosity in only a single dimension, viz. the vertical dimension if one refers to the manufacturing process, and it is thus far from reproducing the bone structure, which is porous in three dimensions in order to facilitate as much as possible the integration of the bone tissue.

Ideally, a surgical implant made of porous titanium whose structure has a controlled pattern, which is repeated in space, in three dimensions, obtained from one of the latest aforementioned methods, for example the LENS process, must have a porosity value of approximately 60%, a pore size on the order of 630 µm and a connection size between pores of 145 µm for the bone colonization to be optimal.

In addition to these properties, an implant of this nature must have mechanical resistance and rigidity characteristics adapted to its use and its environment. Several possible shapes of patterns have thus been computer-analyzed and, following these preliminary scientific analyses, it has been concluded that, theoretically, the rhombic dodecaedron pattern should prove the most efficient.

Numeric simulations on the rhombic dodecaedron pattern have indeed been very conclusive. Such a pattern would theoretically be relatively easy to make in terms of its geometric properties, it would a priori enable good bone colonization of the implant by virtue of its numerous connections between pores and it would possess mechanical characteristics close to those of human cortical bone.

Following these encouraging theoretical results, the applicant of the present patent application has made cubic samples of 10 mm per side by using the method described here-above of selective laser beam bonding, and the samples in question were analyzed.

It turns out that the results obtained in reality are far removed from the theoretical results. Firstly, the geometry of the rhombic dodecaedron thus produced was in fact very uneven in the sense that the beams or branches of the rhombic dodecaedron bond poorly. Many defects in these beams, or even discontinuities, are easily observed through an electronic microscope. Secondly, the structure's mechanical properties are very weak as compared to the mechanical properties that were expected in theory. Thus, from the onset of the mechanical compression tests, the occurrence of compaction and of permanent deformation of the structure were noted. After removing the load, the analyzed samples do not regain their original shape, whatever deformations they have suffered. In other words, the structure starts getting ruined as soon as a force is applied, however small the latter is. The material suffers an irreversible deformation, it is compacted and becomes stiff. Furthermore, the mechanical results recorded, notably the Young module, were very poor, lower by 40% to 60% to those calculated in theory.

The ideal numeric model in the shape of a rhombic dodecaedron is thus far from being perfect. It is the structure itself that explains the poor mechanical properties achieved. Furthermore, again by virtue of the pattern's geometry and notably that of the beams, it is impossible in reality to produce correctly such a pattern with sufficient precision.

All of this has led the applicant to devise another pattern whose geometry would be better suited to the manufacturing process and simultaneously generate mechanical properties better adapted than those of the rhombic dodecaedron.

The present invention thus has as its object a porous structure having a controlled pattern, which is repeated in space, in three dimensions, said porous structure enabling the production of surgical implants for filling in bone defects, characterized in that said pattern consists of three wings arranged in a star shape, each angle formed between two wings being substantially equal to 120°, each wing having a generally rectangular shape and being hollowed at the center thereof.

Advantageously, such a porous structure having a controlled pattern repeated in space is remarkable in that, at its free end or tip, each of the three wings of the pattern is beveled.

In this construction, the width of the base of each bevel formed at the free end of each of the three wings of the pattern is preferably slightly greater than the thickness of said wing.

The porous structure having a controlled pattern repeated in space defined as indicated here-above is advantageously obtained by assembling layers constituted each of a plurality of patterns that, seen in a plan view, are in contact with one another by the sides of the bevels formed at their tips, and is more accurately achieved by the successive superimposition of such layers.

Furthermore, it is possible to vary the mechanical properties and the porosity of such a structure by modifying one of the dimensions of its wings and/or one of the dimensions of its hollows provided at the center of said wings, and this without changing the global shape of the pattern.

By way of first examples, the variable dimension is the height and/or the width and/or the thickness of each wing.

By way of second examples, the variable dimension is the height and/or the width of each hollow.

By way of third examples, the variable dimension is the height and/or the width and/or the thickness of each wing and/or the height and/or the width of each hollow.

In a much-preferred manner, the porous structure having a controlled pattern repeated in space according to the invention is remarkable in that it is made of titanium.

The detailed specifications of the invention are given in the following description in connection with the attached drawings. It must be noted that these drawings have no other purpose than to illustrate the text of the description and that they do not constitute in any way a limitation of the scope of said invention.

FIG. 1 shows the ideal pattern defined in theory, namely the pattern in the shape of a rhombic dodecaedron. In this ideal pattern, the multiple spaces provided between the beams or branches of the dodecaedron render the latter indisputably "open" and are supposed to reproduce the bone's pores and connections between pores.

Figure 1:
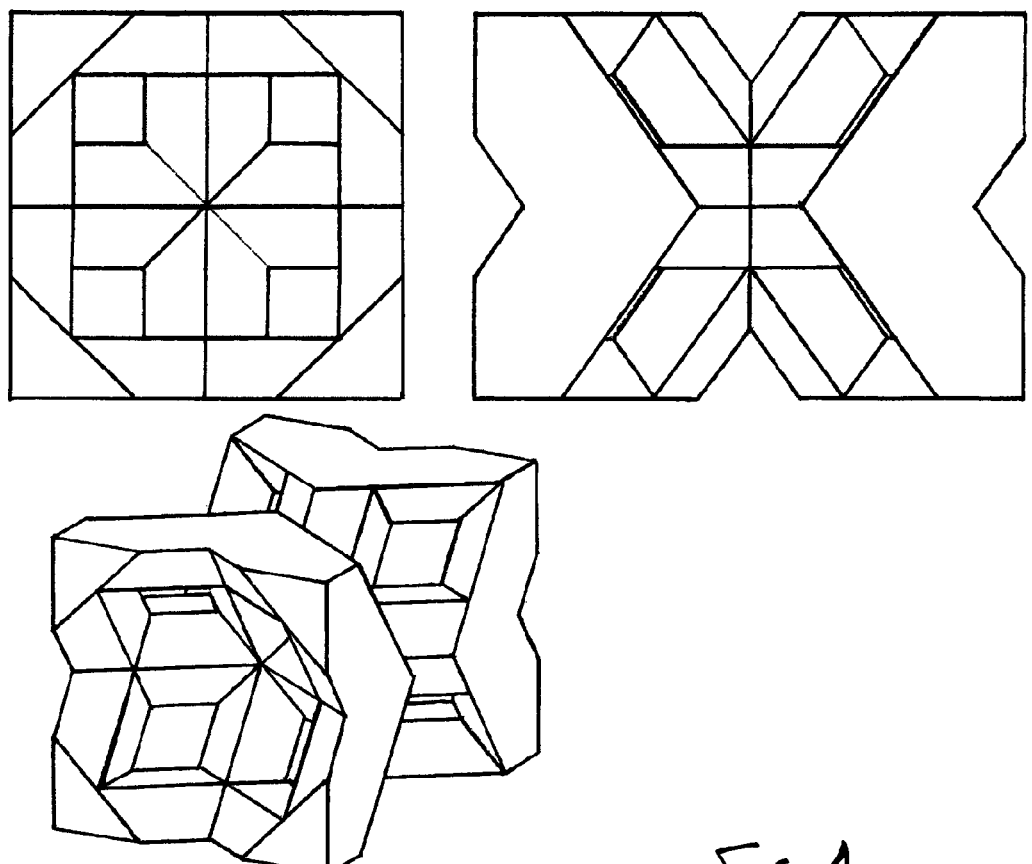
FIG. 1 represents, respectively as a front view, a side view and in perspective, the rhombic dodecaedron which theory claims would constitute the ideal pattern.
Figure 2:
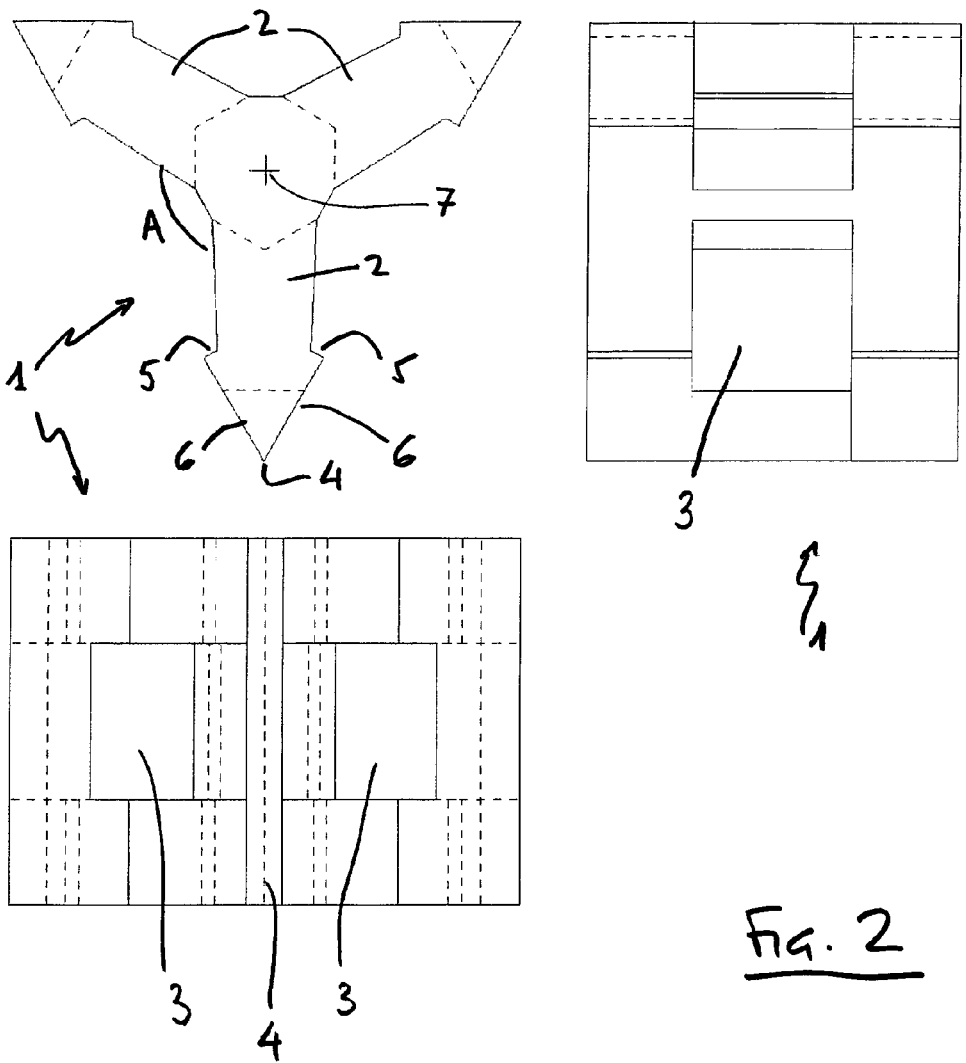
FIG. 2 represents, respectively as a top view, a side view and a front view, the star-shaped pattern proposed according to the present invention.

However, as has been observed in reality, on such rhombic dodecaedron constructions made according to the recommendations in the art, this pattern proves to yield poor results and to be particularly delicate to manufacture, which has led the applicant to search for other patterns, and after studying the results on the other products thus achieved, to select the best one as defined here above and which is represented in detail in FIG. 2.

This basic pattern 1 is essentially constituted of three wings 2 arranged in a star shape, each angle A formed between two wings being substantially equal to 120°.

Each wing 2 has a generally rectangular shape and is hollowed at the center thereof so as to constitute a window or hollow 3.

At its free end, i.e. at its tip 4, each of the three wings 2 of the pattern 1 is beveled and the width of the base 5 of the bevel is slightly greater than the thickness of each wing 2 in order to constitute two projections.

Figure 3:
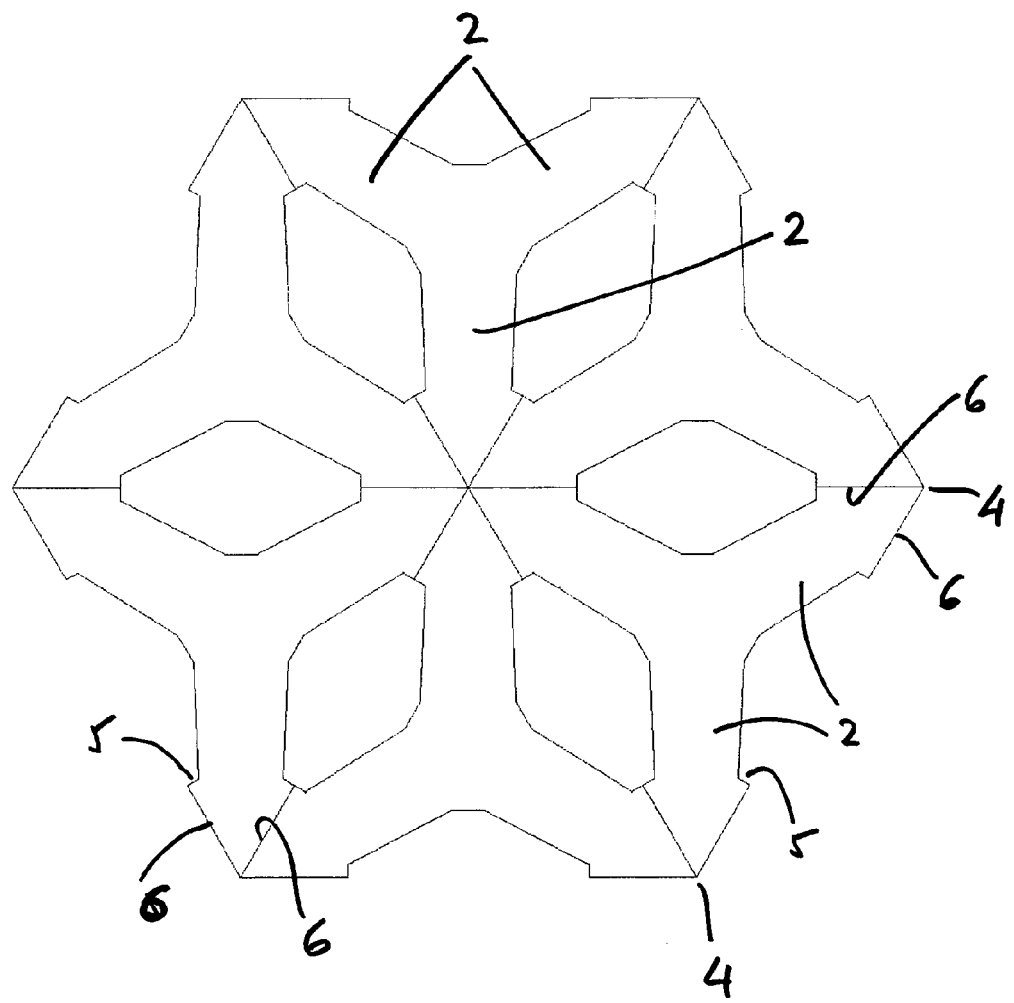
FIG. 3 represents a top view of an assembly of six basic patterns, whose assembly looks like a snowflake.
Figure 4:
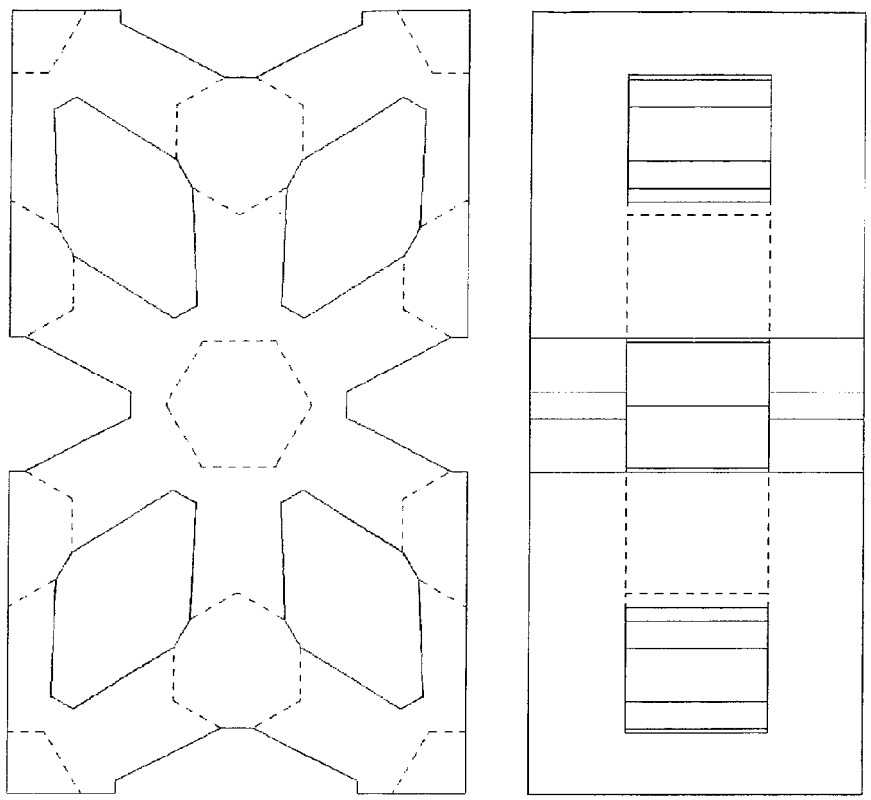
FIG. 4 represents, respectively as a top view, a side view and a front view, an assembly of several basic patterns.
Figure 4:
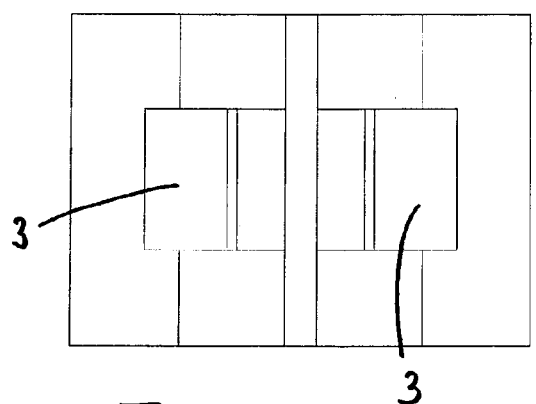

Such a basic pattern is obtained, and repeated in multiple fashion in the two dimensions of the plane, according to the known technique of so-called bonding process by electron beam or by laser beam, by depositing a first layer of titanium powder at the bottom of a tray. It must be observed that the assembly of six basic patterns 1, visible in FIG. 3, thus looks like a snowflake, with the patterns being in contact with one another through the sides 6 of the bevels formed at their different tips 4. In order for the patterns 1 to be in contact by the sides of their tips 4, it is obvious that the angle formed between them by the two sides 6 of each bevel should be equal to 60°.

Once the first layer of titanium powder has been completely bonded according to the geometry of the part to be obtained, a new layer of powder is deposited onto this first layer and is itself bonded at the required places, in order again to reproduce in every circumstance the basic pattern, whilst bonding the patterns of the second layer to those of the first one and again complying with the geometry of the part to be obtained.

The desired part is obtained by repeating the aforementioned operation, by successive superimposition of such layers that are furthermore again bonded to one another.

The particular shape selected by way of basic pattern has the additional advantage of enabling both the size of the pores and the mechanical properties of the finished part to be simultaneously modified by simply varying one or several dimensions of the pattern's wings and/or the hollows 3 provided through the manufacturing process in the wings 2 of said pattern, without however the global shape of the latter being changed.

Figure 5:
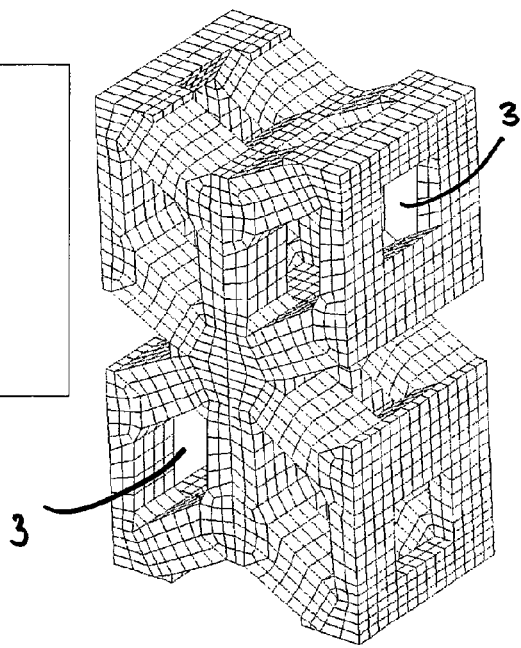
FIG. 5 is a three-dimensional view of the assembly represented in FIG. 4.

FIG. 5 gives an overview of the final part, wherein the multiple basic patterns after assembly generate a structure that makes it possible to fill the space through repetitions, only in the three main directions.

To the best knowledge of the applicant, the star-shaped pattern with three wings as represented and defined hereabove makes it best suited to the production of a bone substitute. In fact, the resulting mechanical properties are those that are closest to those of bone, as compared to the properties of the other patterns that had so far been considered in literature.

By way of a simple example, the star-shaped pattern 1 with three wings is made so as to comply with the following dimensions:

thickness of the wings 2: on the order of 0.50 to 0.60 mm;
distance between two tips 4 of a same pattern: on the order of 2.80 mm;
distance between a tip 4 and the main axis or vertical axis 7 of the pattern: on the order of 1.60 mm;
height of the pattern: on the order of 2 to 3 mm;
height of each hollow 3: on the order of 0.80 to 1.80 mm;
width of each hollow 3: on the order of 0.75 to 0.90 mm;
width of the basis of the bevel: on the order of 0.65 to 0.75 mm.

The invention claimed is:

1. A porous structure for enabling the production of surgical implants for filling in bone defects, the porous structure comprising:
a controlled pattern, repeated in space, in three dimensions, wherein said controlled pattern consists of three wings arranged in a star shape, each of the three wings of the pattern has a bevel at a free end or tip thereof, each angle formed between two adjacent wings being substantially equal to 120°, each wing having a generally rectangular shape in a plane extending substantially perpendicularly to said star shape, and a hollow located at a center of said generally rectangular shape.

2. The porous structure of claim 1, wherein a width of a base of the bevel formed at the free end of each of the three wings of the pattern is slightly greater than a thickness of said wing.

3. The porous structure of claim 1, wherein the structure is obtained by assembling layers constituted each of a plurality of patterns that, in a plane of said star shape, are in contact with one another by sides of the bevels.

4. The porous structure of claim 3, wherein the porous structure is achieved by successive superimposition of such layers.

5. The porous structure of claim 1, wherein the structure is made of titanium.

* * * * *